United States Patent [19]

Junge et al.

[11] Patent Number: 5,702,640
[45] Date of Patent: Dec. 30, 1997

[54] HIGH-MULTIPLEXED SUPERTWIST LIQUID-CRYSTAL DISPLAY

[75] Inventors: Michael Junge, Pfungstadt; Volker Reiffenrath, Rossdorf, both of Germany

[73] Assignee: Merck Patent Gesellschaft Mit Beschrankter Haftung, Darmstadt, Germany

[21] Appl. No.: 607,446

[22] Filed: Feb. 27, 1996

Related U.S. Application Data

[63] Continuation of Ser. No. 346,925, Nov. 23, 1994, abandoned.

[30] Foreign Application Priority Data

Nov. 25, 1993 [EP] European Pat. Off. ............ 93118971

[51] Int. Cl.$^6$ .................... C09K 19/52; G02F 1/1333
[52] U.S. Cl. ..................... 252/299.01; 252/299.61; 252/299.63; 252/299.66; 349/101; 349/180; 349/186
[58] Field of Search ............ 252/299.01, 299.61, 252/299.62, 299.63, 299.64, 299.65, 299.66; 349/101, 180, 186

[56] References Cited

U.S. PATENT DOCUMENTS

| 5,021,189 | 6/1991 | Sawada et al. | 252/299.61 |
| 5,207,944 | 5/1993 | Sawada et al. | 252/299.01 |
| 5,308,538 | 5/1994 | Weber et al. | 252/299.61 |

OTHER PUBLICATIONS

Scheffer et al., "Active Addressing™ of STN displays for high-performance . . . ", Displays, vol. 14, No. 2, 1993, pp. 74–85.

*Primary Examiner*—Shean C. Wu
*Attorney, Agent, or Firm*—Millen, White, Zelano, & Branigan, P.C.

[57] ABSTRACT

The invention relates to improved high-multiplexed supertwist liquid crystal displays in which each pixel is addressed by orthogonal row waver forms, the improvement wherein the nematic liquid crystal mixture consists essentially of 40–80% by weight of at least three compounds having a tolan-4,4'-diyl structure element.

18 Claims, No Drawings

HIGH-MULTIPLEXED SUPERTWIST LIQUID-CRYSTAL DISPLAY

This application is a continuation of application Ser. No. 08/346,925, filed Nov. 23, 1994, now abandoned.

BACKGROUND OF THE INVENTION

The invention relates to high-multiplexed supertwist liquid-crystal displays (SFAs) having extremely short switching times and good steepnesses and angle dependencies, and to the novel nematic liquid-crystal mixtures used therein..

SFAs as in the heading are known, for example from EP 0,131,216 B1; DE 3,423,993 A1; EP 0,098,070 A2; M. Schadt and F. Leenhouts, 17th Freiburg conference on liquid crystals (8-10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784-L1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45; (10), 1021 (1984), M. Schadt and F. Leenhouts, Appl. Phys. Lett. 50 (5), 236 (1987) and E. P. Raynes, Mol. Cryst. Liq. Cryst. Letters, Vol. 4 (1), pp. 1–8 (1986). The term SFA here includes any relatively highly twisted display element having a twist angle with a value between 160° and 720°, such as, for example, the display elements of Waters et al. (C. M. Waters et al., Proc. Soc. Inf. Disp. (New York) (1985) (3rd Intern. Display Conference, Kobe, Japan), the STN-LCDs (DE OS 3,503,259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236, DST-LCDs (EP OS 0,246,842) or BW-STN-LCDs (K. Kawasaki et al., SID 87 Digest 391 (20.6)).

Compared with standard TN displays, SFAs of this type are distinguished by significantly better steepnesses of the electrooptical characteristic and, associated therewith, better contrast values, and by a significantly lower angle dependence of the contrast. Of particular interest are SFAs with extremely short switching times, in particular also at relatively low temperatures. In order to achieve short switching times, the viscosities, in particular of the liquid crystal mixtures have hitherto been optimized using usually optimized combinations of liquid crystal components and optionally also monotropic additives of relatively high vapor pressure. However, the switching times achieved were not adequate for all applications.

Recently (T. J. Scheffer et al. Displays, Vol. 14 (2) 1993 pp. 74–85) a method to address electronically supertwist displays with very short response times has been disclosed. This technique, which is known as Active Addressing, addresses each row of the display for a large proportion of the frame time, unlike the conventional line at a time addressing format, in which each row is addressed only once during each frame with orthogonal wave forms. If the latter, conventional technique is employed in a supertwist LCD with a very short response time, then the general guideline that the refresh time (typically 1.6 ms for a VGA display for a PC) should be 10% of the response time is not observed, thereby leading to a reduction in contrast ratio as a result of the relaxation of the liquid crystal from its "ON" state. Active Addressing has opened the possibility for the addressing of supertwist LCDs, which may enable this simple technology to challenge the high performance high priced levels presently achieved by active matrix addressed liquid crystal displays.

Shorter switching times can also be achieved by reducing the thickness of LC layer of the SFA and using liquid-crystal mixtures with a higher birefringence Δn.

All these approaches to shorter switching times, however, still end up with mixtures which were not adequate for every use.

Further demands for SFA are a higher multiplexability (resulting in a smaller number of IC's), lower threshold voltages and a steep characteristic curve.

Optimal parameters, however, cannot be achieved simultaneously for all the properties mentioned above because of opposite influence of different material parameters such as dielectric and elastic properties.

Therefore, there continues to be a great demand for improved SFAs having short switching times and, at the same time, a broad service-temperature range, low steepness values good angle dependency of the contrast and low threshold voltage.

SUMMARY OF THE INVENTION

The invention has the object of providing SFAs which only have the abovementioned disadvantages to a small extent, or not at all, and at the same time have very useful overall properties.

It has now been found that this object can be achieved if nematic liquid-crystal mixtures are used which contain 40–80 % by weight of three or more compounds having a tolan-4,4'-diyl structure element.

The nematic liquid-crystal mixture preferably has a nematic phase range of at least 60° C., a viscosity of not more than 25 mPa.s, a birefringence of at least 0.200 and a dielectric anisotropy of at least +1, the dielectric anisotropies of the compounds and the parameters related to the nematic liquid-crystal mixture being based on a temperature of 20° C.

The invention thus relates to an high-multiplexed SFA having

- two plane-parallel outer plates which, together with a frame, form a cell,
- a nematic liquid-crystal mixture of positive dielectric anisotropy which is present in the cell,
- electrode layers with superposed alignment layers on the insides of the outer plates which address each pixel by orthogonal row wave forms,
- pre-tilt angle between the longitudinal axis of the molecules at the surface of the outer plates and the outer plates of from about 1 degree to 30 degrees, and
- a twist angle of the liquid-crystal mixture in the cell from alignment layer to alignment layer with a value of between 100° and 600°, wherein the nematic liquid-crystal mixture essentially consists of
  a) 15–50%, preferably 20–50%, by weight of a liquid-crystalline component A, comprising one or more two- or three-ringed compounds having a dielectric anisotropy of more than +1.5;
  b) 0–40% by weight of a liquid-crystalline component B, comprising one or more two- or three-ringed compounds having a dielectric anisotropy from −1.5 to +1.5;
  c) 40–80% by weight of a liquid-crystalline component T, comprising three or more compounds having a tolan-4,4'-diyl structure element, and
  d) an optically active component D in such an amount that the ratio between the layer thickness (separation of the plane-parallel outer plates) and the natural pitch of the chiral nematic liquid-crystal mixture is from about 0.2 to 1.3
and the nematic liquid-crystal mixture has a nematic phase range of at least 60° C., a viscosity of not more than 25 mPa.s. a birefringence of at least 0.1950 and a dielectric anisotropy of at least +1, the dielectric anisotropies of the compounds and the parameters based on the nematic liquid-crystal mixture being based on a temperature of 20° C., characterized in that the component T comprises at least three compounds of formula I

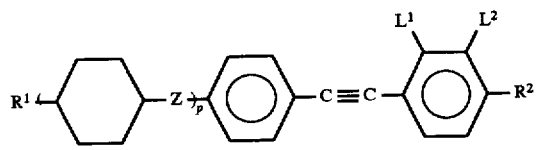

wherein
R¹ is alkyl, alkoxy, alkenyl or alkenyloxy with 1 to 8 C atoms,
L¹ and
L² are each independently H or F,
R² is F, $OCF_3$, alkyl or alkoxy with 1 to 8 C-atoms,
Z is —COO—, —$CH_2CH_2$— or a single bond, and
p is 0 or 1.

Preferably component A contains compounds of the formulae II and III,

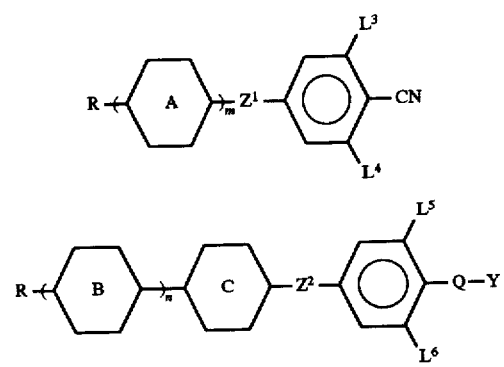

wherein
R is alkyl, alkoxy, alkenyl or alkenyloxy with up to 12 C atoms,

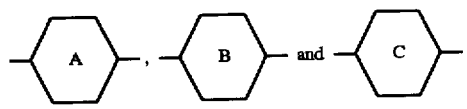

are each independently

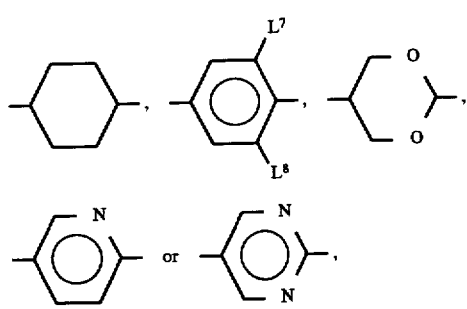

L³ through L⁶ are each independently H or F, $Z^1$ is —COO—, —$CH_2CH_2$— or a single bond,
$Z^2$ is —COO—, —$CH_2CH_2$—, —C≡C or a single bond,
Q is $CF_2$, $OCF_2$, CFH, OCFH or a single bond,
Y is F or Cl,
m is 1 or 2, and
n is 0 or 1.

Component A is, in particular, selected from the formulae IIa to IId:

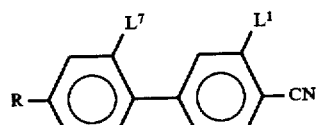

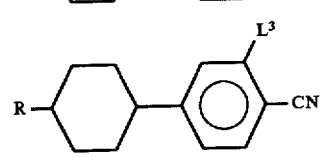

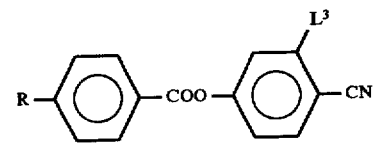

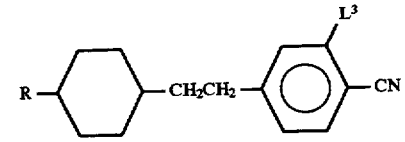

wherein R and L¹ have the meaning given.

Another aspect of the invention is the use of compounds of formula Ia1

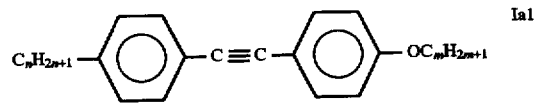

wherein n and m have the meaning given for the improvement of the switching times and steepness of STN-displays of which each pixel is addressed by an orthogonal row wave form.

The individual compounds of the formulae I, II and III and also other compounds which can be used in the SFAs according to the invention, are either known or can be prepared analogously to the known compounds.

The compounds of formula I are known from U.S. Pat. No. 3,925,482 and WO 88/07514 but there is no hint that the switching times of high-multiplexed SFA's can be improved with their aid.

GB-A-2 255 465 discloses mixtures of a two-ring or three-ring tolan with component (A) type liquid crystal where it is possible to add a component (B) type liquid crystal. However a Δn of only 0.133 can be achieved.

A liquid crystal composition aiming at increasing Δn by using a tolan liquid crystal compound having a large Δn is disclosed in Japanese Patent Disclosure Nos. 61-97383 and 61-97384, and EP 178937. These liquid crystal compositions mainly contain a tolan liquid cyrstal compound having a large Δn, a liquid crystal compound having an ester bond, and component (A) type liquid crystal compound having a cyano group at its terminal and a large Δε.

Since such a conventional liquid crystal composition contains a tolan liquid crystal compound having a large Δn, the optical anisotropy of the resultant composition is relatively large. In addition, since the compound having an ester bond is contained in the composition, a smectic phase tends not to appear in a low-temperature atmosphere. A phenyl cyclohexanecarboxylate liquid crystal compound having the ester bond has a small Δn, and therefore the optical anisotropy of the composition is not so high (about 0.175 at most). The liquid crystal compound having the ester bond has a relatively high viscosity among liquid crystal compounds having a low viscosity. For example, the liquid crystal compound having the ester bond has a viscosity of about 20 cp. For this reason, the viscosity of the liquid crystal composition containing such a liquid crystal compound has a high viscosity, e.g., 28 cp or more.

EP 0 268 226 discloses mixtures of two-ring and three-ring tolan with more than 20% of two-ring component (B) type liquid crystals for low or middle multiplex TN applications as can seen from the low clearing points of about 55° to 65° C. These are typically used for handheld calcualators or video games. Those mixtures are characterized by very low steepnesses in the devices of typically 85%.

To the contrary the mixtures of this invention allow the realization of high-multiplexed SFAs with very high multiplex ratios, broad working temperature range, low threshold voltages (below 3 volt, preferably between 1.25 and 2.80, in particular between 1.60 and 2.20 volt) and steep characteristic curves and high clearing points of more than 75° C., preferably 76° to 110° C. in particular 90° C. to 100 ° C.

The compounds of the formulae I, II and III have low viscosities, in particular low rotational viscosities, low values of the ratio of the elastic constants ($K_3/K_1$) and lead therefore to short switching times.

The mixtures according to the present invention have an optic anisotropy (Δn) of more than 0.200, preferably 0.201–0.270, in particular 0.220–0.250.

The mixtures according to the invention preferably contain one or more compounds of formula II and/or formula III selected from the following group:

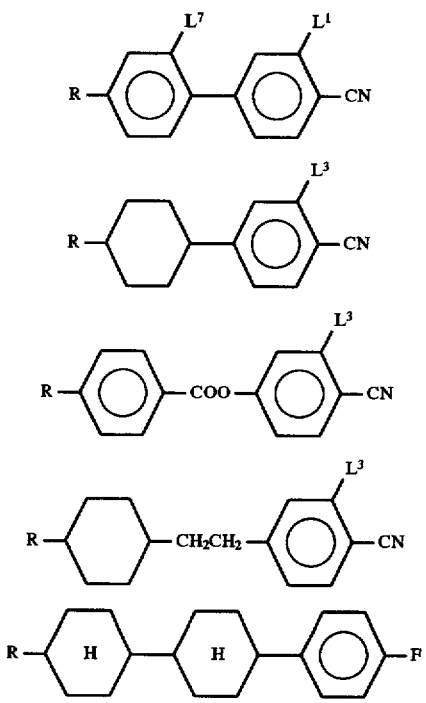

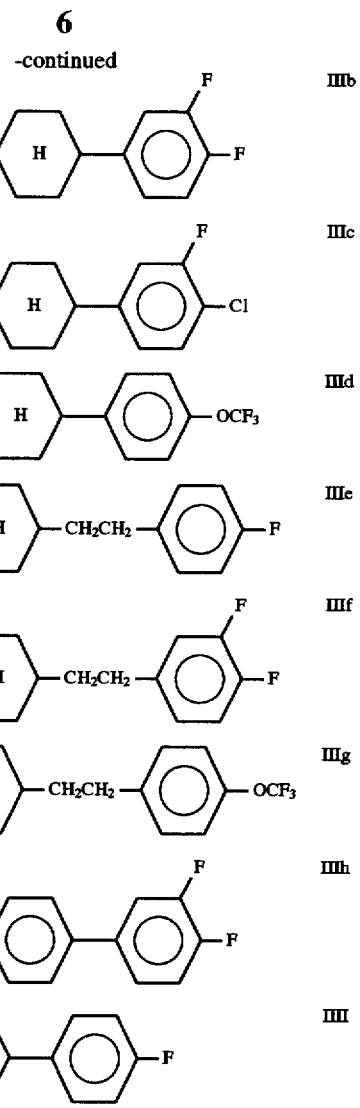

wherein R, $L^3$ and $L^7$ have the meaning given.

Preferred mixtures contain two or more compounds of the formulae IIa, IIb, IIc, IId, IIIh, in particular one or more compounds of the formula IIa or IIb and three to six compounds of formula I.

Preferred liquid-crystal mixtures which can be used according to the invention contain one or more compounds from group A preferably in a proportion of 20% to 50%, preferably 22% to 40%. These compounds or this compound from group A have a dielectric anisotropy of more than +3 (preferably of more than +8, in particular more than +12) and form the component A of the LC mixtures of this invention.

Preferably the mixtures comprise one ore more compounds of the formula II in the range of 22% to 40%. Preferred are those compounds wherein $Z^1$ denotes a single bond, —CH₂CH₂— or —CO—O— and especially preferred are the following compounds:

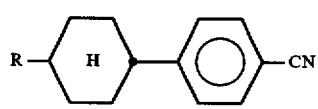

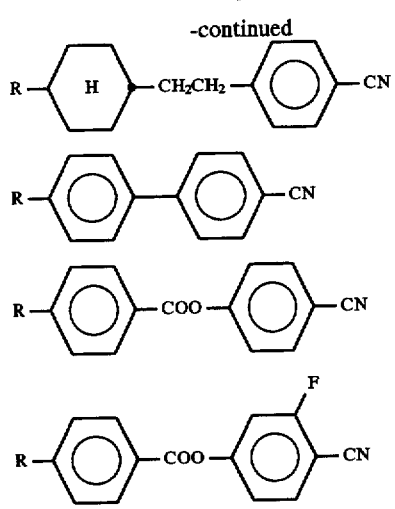

Also preferred are the following compounds:

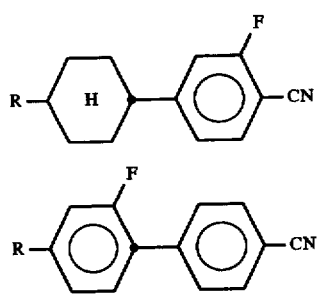

Group A preferably comprises one ore more compounds selected from the formulae IIb1 to IIc1 and optionally also one or more compounds of the formula IIc2.

Preferably the mixtures further contain one or more polar compounds with a higher clearing point, e.g. selected from the following compounds:

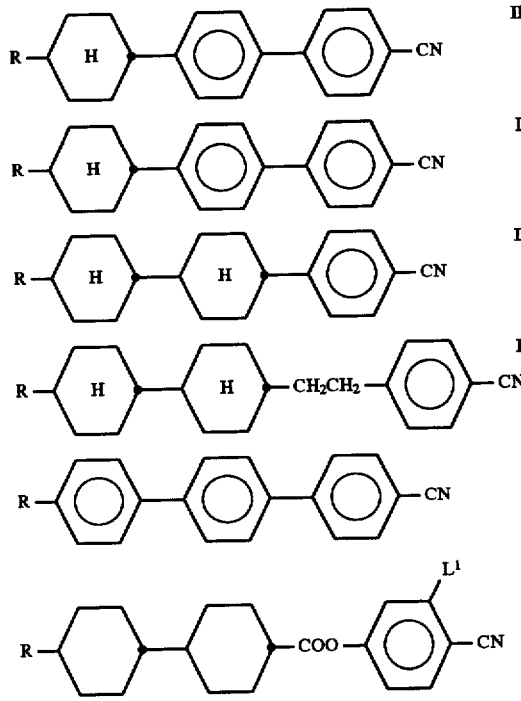

In the above four formulae the 1.4-phenylene rings can also be laterally substituted by one fluorine atom, e.g.

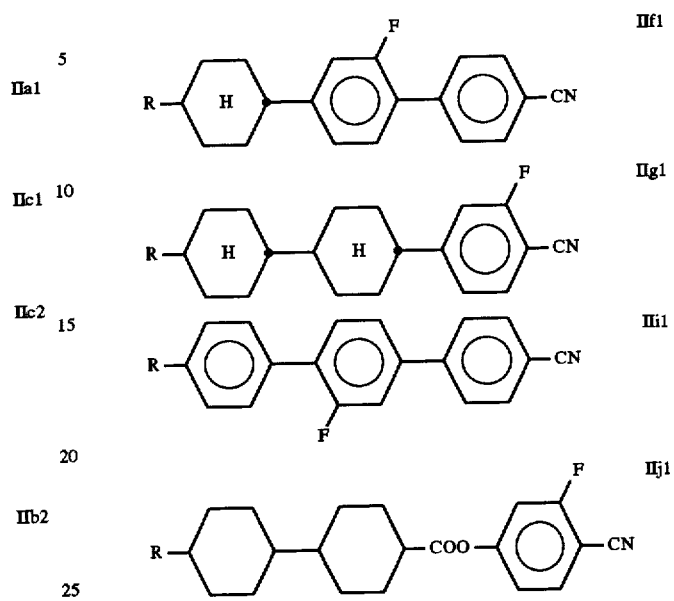

These polar compounds with a higher clearing point are preferably used in the range of 2 to 25%.

In another preferred embodiment the mixtures comprise one or more compounds with a very high dielectric anisotropy. Such compounds are preferably used in the range of 2 to 15%. Preferred compounds of this type are those of the formulated, IIc2 and III1.

Preferred liquid-crystal mixtures contain one or more compounds from group B, preferably in a proportion of 0 to 25%. These compounds or this compound from group B have either low values of the rotational viscosity ($\gamma 1$)<150 mPa.s or a clearing point of more than 120° and are dielectrically neutral (($\Delta\epsilon$)<2) in particular 0 to 10) and form component B of the LC mixtures of this invention.

Preferably component B contains one or more compounds selected from the group comprising IV1 to IV 7 with two rings:

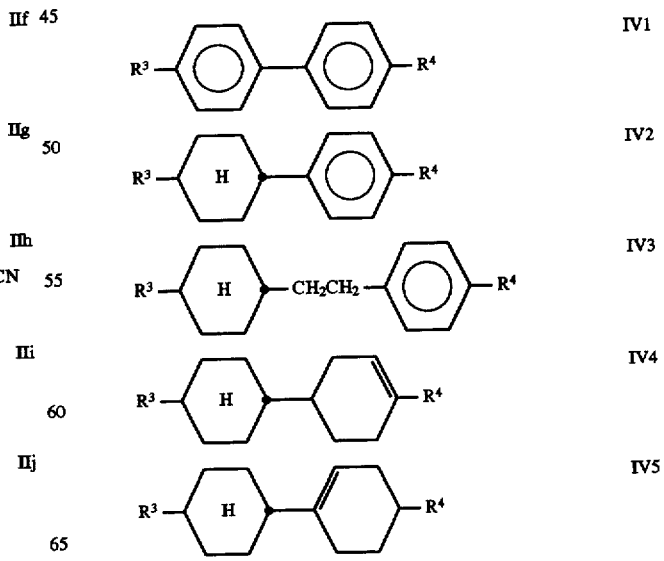

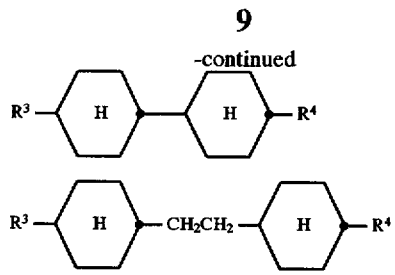

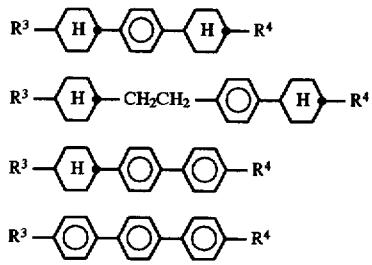

in which $R^3$ and $R^4$ have the meaning given for R and/or one or more compounds selected from the group comprising IV8 to IV21 with three rings:

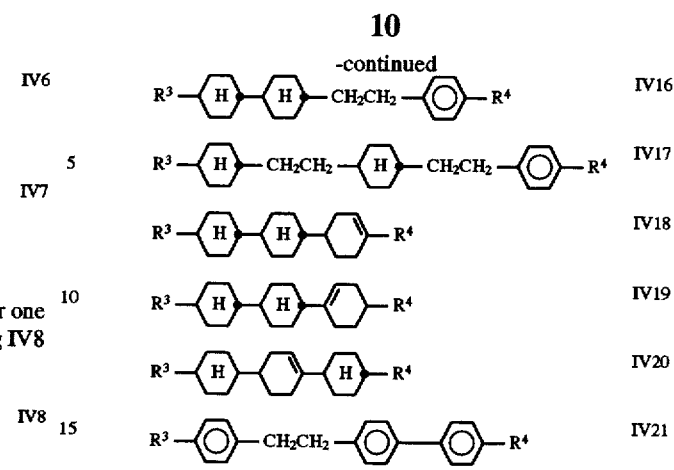

in which $R^3$ and $R^4$ have the meaning given, the 1,4-phenylene groups IV7 to IV17 and IV21 may each, independently of one another, also be mono- or polysubstituted by fluorine. In the case that component B, comprises more than 10% of one or more two-ringed compound the nematic mixture additionally contains one or more, preferably only one, compounds selected from the group comprising IV22 to IV27:

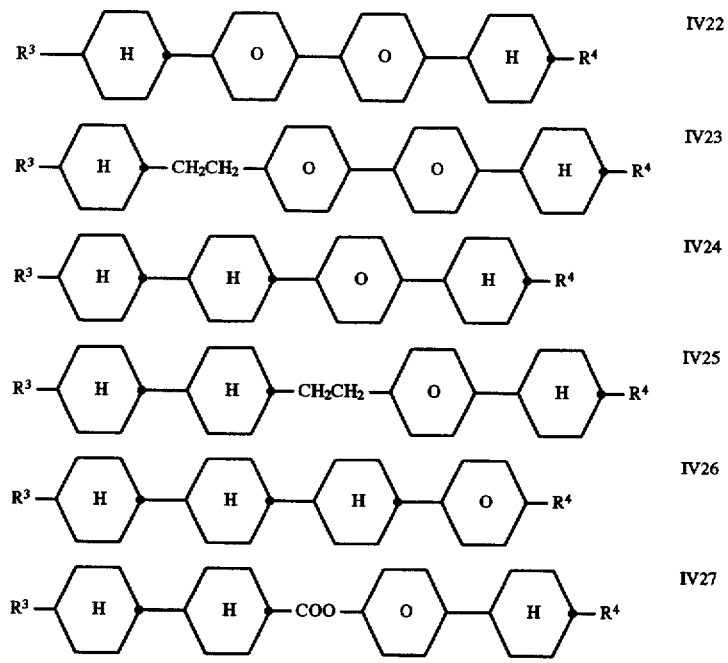

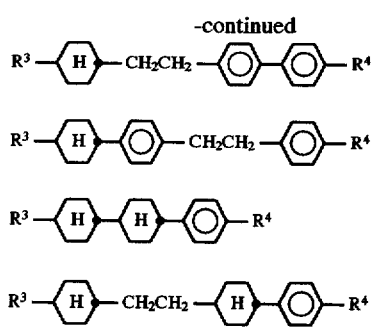

in which $R^3$ and $R^4$ have the meaning given, and the 1,4-phenylene groups in IV22 to IV27 may each, independently of one another, also be mono- or polysubstituted by fluorine.

In any event the nematic mixture contains only up to 5% by weight, preferably 0 to 4% by weight of one or more compounds of the formulae IV22 to IV27.

The LC mixtures also comprise an optically active component C, in an amount such that the ratio between the layer thickness (separation of the plane-parallel carrier plates) and the natural pitch of the chiral nematic liquid crystal mixture is more than 0.2 suitable to the desired twist angle. Suitable dopants can be selected from a wide variety of known chiral materials and commercially available dopants such as cholesteryl nonanoate, S 811 (E. Merck, Darmstadt, FRG) and CB 15 (Merck Ltd., former, BDH, Poole, UK). The choice thereof is not crucial per se.

In a further preferred embodiment the LC mixtures contain five or more compounds selected from the group comprising Ia to Ie:

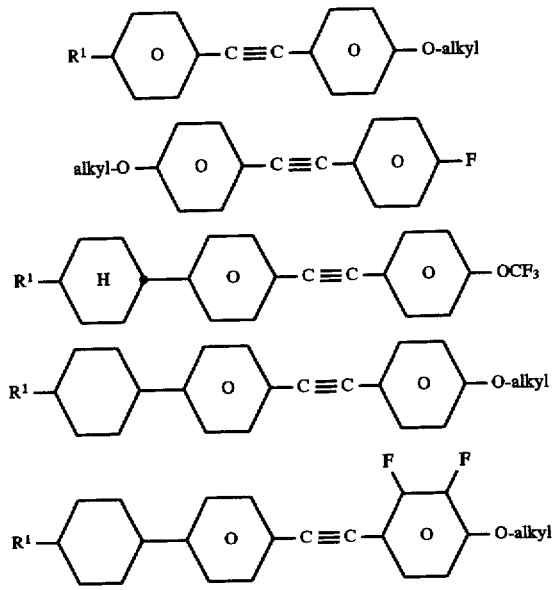

in which R¹ has the meaning given and alkyl is n-alkyl with 1 to 8 C atoms.

The proportion of component(s) from group T is preferably 40% to 80%, in particular 42% to 65%.

The proportion of two-ringed tolans of formulae Ia and Ib is preferably 16 to 60% and the proportion of three-ringed tolans of formulae Ic to Ie is preferably 18 to 35%.

The total proportion of all terminally fluorinated non-tolan type compounds is preferably about 5% to 25%, in particular about 10% to 20%.

The proportion of compounds of an additional component C comprising one or more compounds having a dielectric anisotropy<−1.5 is preferably about 0% to 20%, in particular about 0% to 10%. Those skilled in the art can easily adjust this proportion to produce the threshold voltage desired, it being possible to use, in principle, all customary liquid-crystal compounds where Δε<−1.5.

In a particularly preferred embodiment, the mixtures according to the invention preferably contain about 0% to 10% of one or more compounds having a dielectric anisotropy of less than −2 (component C). Compounds of this type are known, for example derivatives of 2,3-dicyanohydroquinone or cyclohexane derivatives containing the structural element

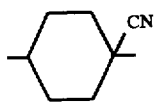

as in DE-OS 3,231,707 or DE-OS 3,407,013.

However, compounds containing the structural element 2,3-difluoro-1,4-phenylene are preferably chosen, for example compounds as in DE-OS 3,807,801,3,807,861,3, 807,863, 3,807,864 or 3,807,908. Particularly preferred are tolans containing these structural elements, as in International Patent Application PCT/DE 88/00133, in particular those of the formulae

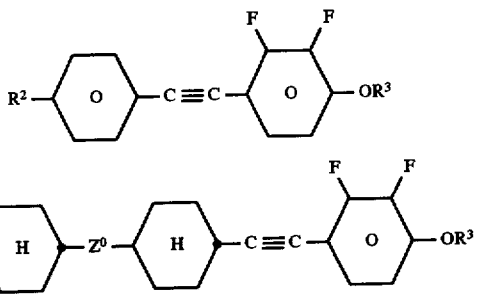

in which R² and R³, in each case independently of one another, are preferably n-alkyl having 1 to 7 C atoms or n-alkenyl having 3 to 7 C atoms, and Z° is —CH₂CH₂— or a single bond.

Particularly preferred are also the phenylcyclohexylcarboxylates of the formulae

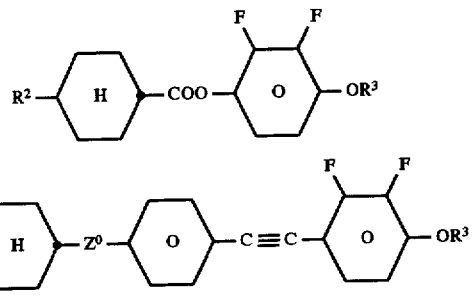

where

R³ is n-alkyl or n-alkoxy, each having 1 to 7 C atoms, or n-alkenyl or n-alkenyloxy, each having 3 to 7 C atoms.

Preferably component T contains one or more compounds of the formula T3

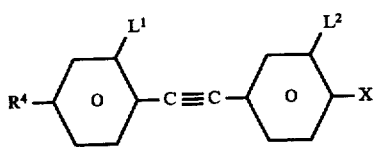

in which

R⁴ is —C$_{nH2n+1}$, —OC$_n$H$_{2n+1}$,

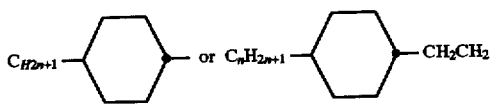

n is an integer from 1 to 15,

L¹ and L² are each, independently of one another, H or F, and

X is F, Cl or OCF₃.

In further particularly preferred embodiments, the mixtures contain

15–60% by weight of two or more compounds of formula I, wherein p is 0, in preferably at least two compounds of formulae Ia and/or Ib, in particular one to five compounds of formula Ia1

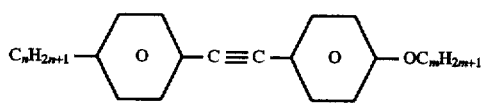

Ia1 wherein m is 1 or 2 and n is an integer of 1 to 7, preferably 1 or 2,

10–40% by weight of two or more compounds of formula I, wherein p is 1, preferably at least two compounds of formula Id and/or Ie, a component C which contains one or more compounds having a 1-cyano-trans-1,4-cyclohexylene group or a 2,3-difluoro-1,4-phenylene group, at least one compound from the following group:

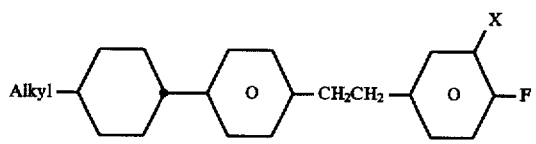

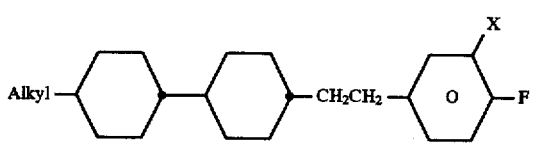

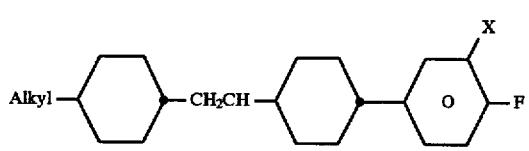

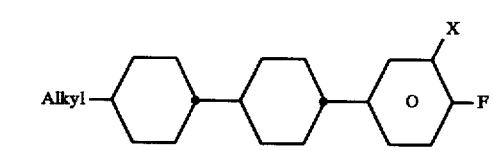

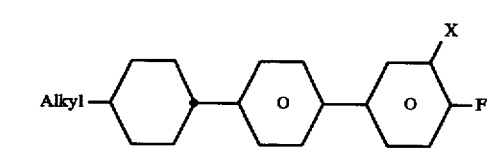

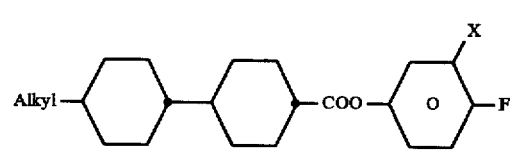

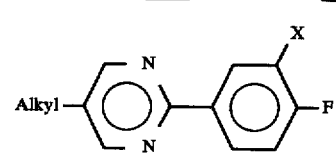

in which alkyl is a straight-chain alkyl group having 2–7 C atoms, and X is H or F, one or more compounds in which R is a trans-alkenyl group or a trans-alkenyloxy group, one or more compounds selected from the following group

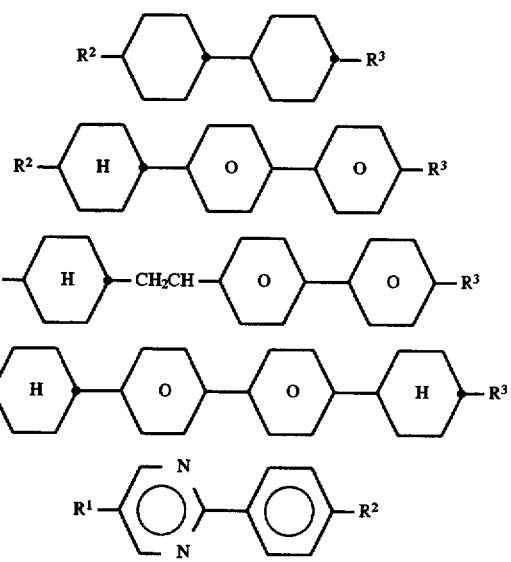

in which $R^2$ and $R^3$ have the preferred meanings indicated in the case of component B, and one of the two 1,4-phenylene groups may also be substituted by fluorine; the proportion of these compounds is 0% to 25%, preferably about 5% to 15%.

In a further particularly preferred embodiment the mixtures contain at least two compounds selected from the formulae IIb1, IIc1 or IIc2.

two or more compounds of the formulae Ia or Ib or one or more compounds selected from the following group

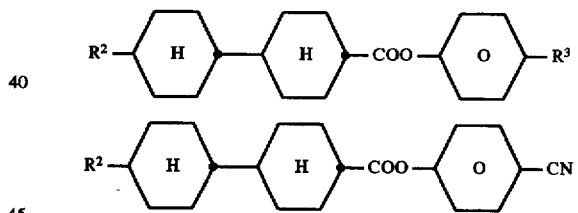

wherein $R^2$ and $R^3$ are defined as for the compounds of the formula III.

In a further preferred embodiment the mixtures contain
15–50% by weight of a liquid crystalline component A, which essentially consists of compounds of formula III, in particular of compounds of formula IIIs, and at least
30–50% by weight of at least one compound of formula I, wherein $R^2$ is F or $OCF_3$.

The construction of the liquid-crystal display elements according to the invention from polarizers, electrode base plates and electrodes having a surface treatment such that the preferential orientation (director) of the liquid-crystal molecules in each case adjacent thereto is usually mutually twisted from one electrode to the other by a value of 160° to 720°, corresponds to the customary construction for display elements of this type. The term customary construction here is used in broad terms and also includes all derivatives and modifications of supertwist cells, in particular also matrix display elements. The surface tilt angle at the two support plates may be identical or different. Identical tilt angles are preferred.

The inventive display is addressed by orthogonal wave forms as described, for example, by T. J. Scheffer et al., Displays Vol 14(2) 1993 pp. 74–85.

An essential difference between the display elements according to the invention and the display elements customary hitherto based on the twisted nematic cell is, however, the choice of liquid-crystal components in the liquid-crystal layer.

The liquid-crystal mixtures which can be used according to the invention are prepared in a manner customary per se. In general, the desired amount of the components used in a relatively small amount is dissolved in the components making up the principal constituent, expediently at elevated temperature. It is also possible to mix solutions of the components in an organic solvent, for example in acetone, chloroform or methanol, and to remove the solvent again, after mixing, for example by distillation.

The dielectrics may also contain further additives known to those skilled in the art and described in the literature, for example, 0–15% of pleochroic dyes may be added.

The examples which follow are intended to illustrate the invention without limiting it.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding European Application 93118971.6, filed Nov. 25, 1993, are hereby incorporated by reference.

EXAMPLES

The abbreviations in the examples have the following meanings:

| | |
|---|---|
| S-N | smectic-nematic phase transition temperature, |
| N-I | nematic-isotrop phase transition temperature, |
| c.p. | clear point, |
| visc. | viscosity (m Pa · s), |
| $T_{ave}$ | average switching time $= \dfrac{T_{on} + T_{off}}{2}$ |
| $T_{on}$ | time from switching on until 90% of the maximum contrast is reached, |
| $T_{off}$ | time from switching off until 10% of the maximum contrast is reached, |
| $V_{10}$ | threshold voltage (volt) |
| $V_{90}$ | saturation voltage |
| $V_{90}/V_{10}$ | steepness |

The SFA is addressed with an orthonormal wave form (multiplex ratio 1:256, bias 1:16, operating voltage 7.2 volts).

The values for the switching times and viscosities relate to 20° C.

In the present patent application and in the following examples all chemical structures of LC compounds are given by acronyms the transformation of which into chemical formulae is done as shown in the following. All residues $C_nH_{2n+1}$ and $C_mH_{2m+1}$ are straight-chained alkyl groups with n resp. m carbon atoms. The code of Table B is self-explanatory. In Table A only the acronym for the core structure is given. In a concrete compound this acronym is followed by a dash and a code for the substituents $R^1, R^2, L^1$ and $L^2$ as follows:

The compounds given in Tables A and B are particularly preferred components of the present invention.

| Code for $R^1$, $R^2, L^1, L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | F |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nNf | $C_nH_{2n+1}$ | CN | F | H |
| nAm | $C_nH_{2n+1}$ | $COOC_mH_{2m+1}$ | H | H |
| nF.Cl | $C_nH_{2n+1}$ | Cl | H | F |

TABLE A

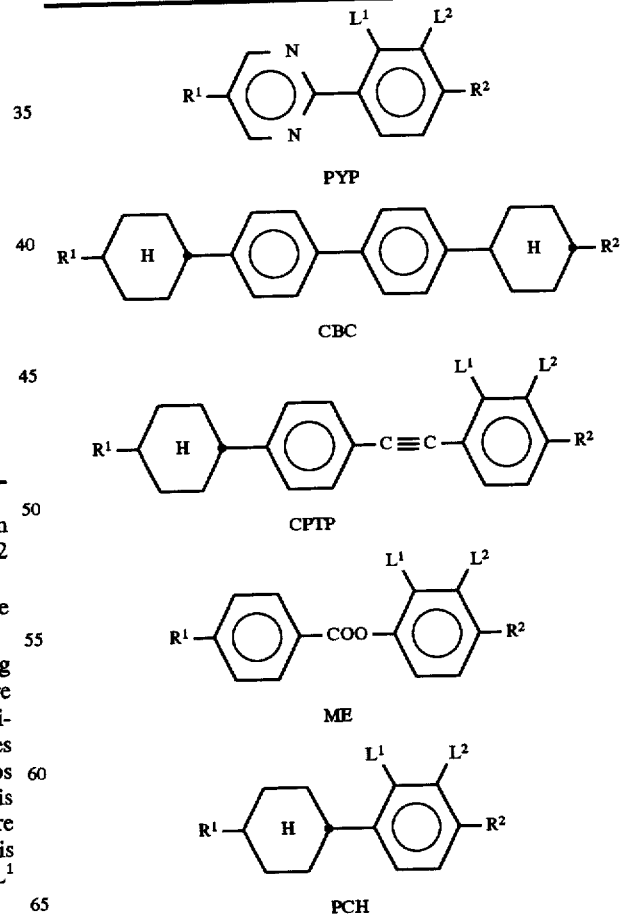

PYP

CBC

CPTP

ME

PCH

TABLE A-continued
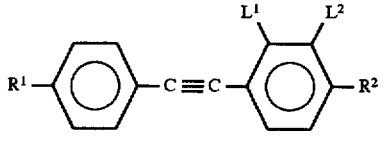
PTP
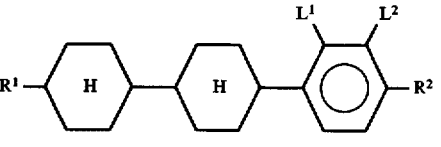
BCH
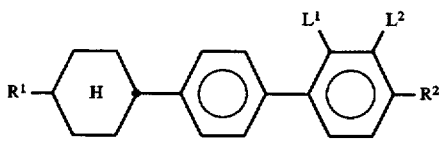
CP
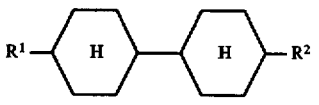
CPP
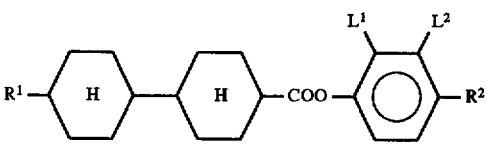
CCH
TABLE B
K3n
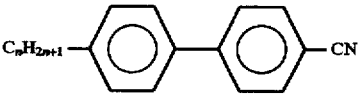
Inm
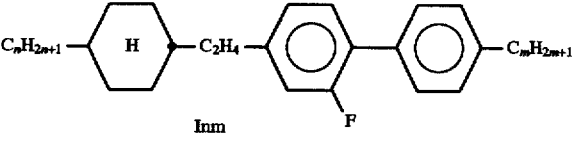
S-811
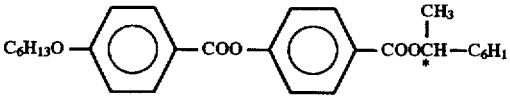
C15
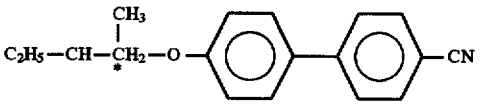
CB15

TABLE B-continued

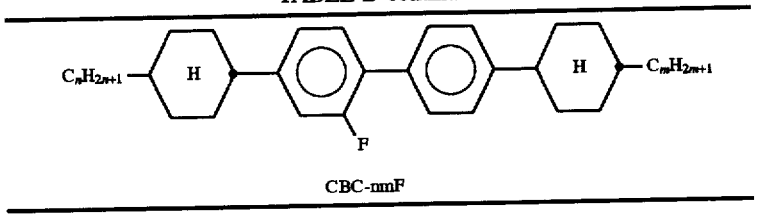

CBC-nmF

Example 1

A STN display with the following parameters:

| | |
|---|---|
| twist angle | 240° |
| bias | 1:16 |
| multiplex rate | 1:256 |
| frame rate | 80 Hz |
| tilt angle | 5° |
| d | 4.2 μm | contains a liquid crystalline medium with the following properties:

| | |
|---|---|
| S—N | <−30° |
| N—I | 95 |
| Δn | 0.2024 |
| γrot | 75 mPa · s | consisting of an achiral base mixture:

| | |
|---|---|
| PCH-3 | 13.0 |
| K6 | 10.0 |
| PCH-301 | 18.0 |
| PCH-302 | 7.0 |
| CPTP-301 | 6.0 |
| CPTP-302 | 6.0 |
| CPTP-303 | 6.0 |
| CPTP-30CF3 | 6.0 |
| CPTP-50CF3 | 6.0 |
| PTP-102 | 6.0 |
| PTP-201 | 6.0 |
| PTP-20F | 6.0 |
| CBC-33 | 4.0 | and being doped with 1.07% of S-811 and being addressed with orthogonal row wave forms shows the following switching parameters:

| | |
|---|---|
| $T_{ave}$ | 140 ms |
| $V_{10}$ | 2.33 V |
| $V_{90}/V_{10}$ | 1.056 |

Example 2

A STN display as described in Example 1 with d=3.5 μm containing a liquid crystalline medium with the following parameters:

| | |
|---|---|
| S—N | <−30° C. |
| N—I | +96° C. |
| Δn | 0.2444 |
| γrot | 95 mPa · s | consisting of an achiral base mixture:

| | |
|---|---|
| PCH-3 | 18.0 |
| K6 | 9.0 |
| K9 | 9.0 |
| PTP-20F | 8.0 |
| PTP-40F | 7.0 |
| PTP-302FF | 8.0 |
| PTP-502FF | 8.0 |
| CPTP-302FF | 9.0 |
| CPTP-502FF | 9.0 |
| CPTP-301 | 5.0 |
| CPTP-302 | 5.0 |
| CPTP-303 | 5.0 | being doped with 1.30% of S-811 shows the following switching parameters:

| | |
|---|---|
| $T_{ave}$ | 140 ms |
| $V_{10}$ | 2.09 V |
| $V_{90}/V_{10}$ | 1.028 |

Example 3

A STN display as described in Example 1 with d=3.75 μm containing a liquid crystalline medium with the following properties:

| | |
|---|---|
| S—N | <0° C. |
| N—I | +78 |
| Δn | 0.2267 |
| γrot | 70 mPa · s | consisting of an achiral base mixture:

| | |
|---|---|
| K6 | 8.00 |
| k9 | 8.00 |
| PYP-5F | 10.00 |
| PCH-3 | 13.00 |
| PCH-301 | 6.00 |
| PTP-20F | 8.00 |
| PTP-40F | 7.00 |
| PTP-102 | 5.00 |
| PTP-201 | 6.00 |
| CPTP-302FF | 5.00 |
| CPTP-502FF | 5.00 |
| CPTP-301 | 5.00 |
| CPTP-302 | 5.00 |
| CPTP-303 | 5.00 |
| CPTP-30CF3 | 4.00 | being doped with 1.43% of S-811 shows the following switching parameters:

| | |
|---|---|
| $T_{ave}$ | 102 ms |
| $V_{10}$ | 1.92 V |
| $V_{90}/V_{10}$ | 1.068 |

Example 4

A STN display as described in Example 1 containing a liquid crystalline medium with the following properties:

| | |
|---|---|
| S—N | <0° |
| N—I | +85° |
| $\Delta n$ | 0.2416 | consisting of an achiral base mixture:

| | |
|---|---|
| PTP-501 | 12.0 |
| PTP-502 | 11.0 |
| PTP-504 | 6.0 |
| PTP-102 | 5.0 |
| PTP-201 | 6.0 |
| PTP-20F | 6.0 |
| PTP-40F | 5.0 |
| PTP-60F | 5.0 |
| PCH-3 | 12.0 |
| PCH-4 | 12.0 |
| CPTP-302FF | 5.0 |
| CPTP-502FF | 5.0 |
| CPTP-301 | 5.0 |
| CPTP-302 | 5.0 | and being doped with 1.46% of S-811 shows the very fast switching times and high mugltiplexibility.

Example 5

A STN display as described in Example 1 containing a liquid crystalline medium with the following properties:

| | |
|---|---|
| S—N | <0° |
| N—I | 85 |
| $\Delta n$ | 0.2398 | consisting of an achiral base mixture:

| | |
|---|---|
| PTP-501 | 22.0 |
| PTP-502 | 11.0 |
| PTP-504 | 6.0 |
| PTP-201 | 6.0 |
| PTP-20F | 6.0 |
| PTP-40F | 5.0 |
| PCH-3 | 12.0 |
| PCH-4 | 12.0 |
| CPTP-302FF | 5.0 |
| CPTP-502FF | 5.0 |
| CPTP-301 | 5.0 |
| CPTP-302 | 5.0 | and being doped with 1.55% of S-811 shows the very fast switching times and high multiplexibility.

Comparative Example 1

A STN display as described in Example 1 contains a medium with the following properties:

| | |
|---|---|
| S—N | −30 |
| N—I | +91° |
| $\Delta n$ | 0.2077 |
| $\gamma_{rot}$ | 116 mPa·s | consisting of

| | |
|---|---|
| PCH-3 | 10.0 |
| PCH-5 | 8.0 |
| ME2N.F | 2.0 |
| ME3N.F | 2.0 |
| ME5N.F | 4.0 |
| PTP-20F | 9.0 |
| PTP-40F | 9.0 |
| PTP-60F | 6.0 |
| PTP-102 | 5.0 |
| PTP-201 | 6.0 |
| CPTP-301 | 6.0 |
| CPTP-302 | 4.0 |
| CPTP-303 | 6.0 |
| PCH-301 | 11.0 |
| CBC-33F | 4.0 |
| CBC-55F | 4.0 |
| CBC-55F | 4.0 | and being doped with 1.27% of S-811 shows the following switching parameters:

| | |
|---|---|
| $T_{ave}$ | 168 ms |
| $V_{10}$ | 2.12 V |
| $V_{90}/V_{10}$ | 1.058 |

This comparison clearly shows that high amounts of two-ringed component B type LC's (PCH-301) combined with more than 5% of four-ringed LC's (CBC-nmF) yield slow switching times.

Example 6

A STN display as described in Example 1 containing a liquid crystalline medium with the following properties

| | |
|---|---|
| N—I | 91 |
| $\Delta n$ | 0.2305 | consisting of an achiral base mixture:

| | |
|---|---|
| PTP-20F | 13.0 |
| PTP-40F | 13.0 |
| PTP-60F | 13.0 |
| PCH-302 | 18.0 |
| PTP-102 | 5.0 |
| PTP-201 | 5.0 |
| CPTP-301 | 5.0 |
| CPTP-302 | 4.0 |
| CPTP-303 | 5.0 |
| BCH-3F.F | 8.0 |
| BCH-5F.F | 8.0 |
| CBC-53F | 8.0 | and being doped with S-811 shows very fast switching times and

| | |
|---|---|
| $V_{10}$ | 3.28 V |
| $V_{90}/V_{10}$ | 1.326 |

Examples 7 to 11

A STN display as described in Example 1 containing a liquid crystalline mixture of which the properties and compositions are shown in the following table show very fast switching times and high multiplexibility.

TABLE I

| | Example 7 | | Example 8 | | Example 9 | | Example 10 | | Example 11 | |
|---|---|---|---|---|---|---|---|---|---|---|
| Clearing point [°C.] | +106 | | +102 | | +97 | | +99 | | +99 | |
| $\Delta n$ | +0.2464 | | +0.2479 | | +0.2368 | | +0.2291 | | +0.2239 | |
| (589 nm, 20° C.) | | | | | | | | | | |
| $n_e$ (589 nm, 20° C.) | 1.7501 | | 1.7536 | | 1.7455 | | 1.7359 | | 1.7304 | |
| $V_{10}$ | 2.73 | | 2.59 | | 2.28 | | 2.37 | | — | |
| $V_{90}/V_{10}$ | 1.0734 | | 1.0721 | | 1.0655 | | 1.0544 | | — | |
| Composition [%]: | PCH-3 | 22.0 | PCH-3 | 22.0 | PCH-3 | 30.0 | PCH-3 | 30.0 | PCH-3 | 30.0 |
| | PTP-102 | 4.0 | PTP-102 | 4.0 | PTP-102 | 4.0 | PTP-102 | 4.0 | PTP-102 | 4.0 |
| | PTP-201 | 4.0 | PTP-201 | 4.0 | PTP-201 | 4.0 | PTP-201 | 4.0 | PTP-201 | 4.0 |
| | PTP-501 | 15.0 | PTP-501 | 13.0 | PTP-501 | 13.0 | PTP-501 | 10.0 | PTP-501 | 8.0 |
| | PTP-502 | 15.0 | PTP-502 | 13.0 | PTP-502 | 13.0 | PTP-502 | 10.0 | PTP-502 | 8.0 |
| | PTP-504 | 10.0 | PTP-20F | 7.0 | PTP-20F | 5.0 | PTP-20F | 5.0 | PTP-20F | 5.0 |
| | CPTP-301 | 6.0 | PTP-40F | 7.0 | PTP-40F | 5.0 | PTP-40F | 5.0 | PTP-40F | 5.0 |
| | CPTP-302 | 6.0 | CPTP-301 | 6.0 | CPTP-301 | 7.0 | CPTP-301 | 7.0 | CPTP-301 | 7.0 |
| | CPTP-303 | 6.0 | CPTP-302 | 6.0 | CPTP-302 | 8.0 | CPTP-302 | 8.0 | CPTP-302 | 8.0 |
| | CPTP-30CF3 | 6.0 | CPTP-303 | 6.0 | CPTP-303 | 7.0 | CPTP-303 | 7.0 | CPTP-303 | 7.0 |
| | CPTP50CF3 | 6.0 | CPTP-30CF3 | 6.0 | CPTP-30CF3 | 4.0 | CPTP-30CF3 | 4.0 | CPTP-30CF3 | 4.0 |
| | | | CPTP50CF3 | 6.0 | | | I32 | 6.0 | I32 | 10.0 |

Examples 12 to 18

A STN display as described in Example 1 containing a liquid crystalline mixture of which the properties and compositions are shown in the following table:

TABLE II

| | Example 12 | | Example 13 | | Example 14 | | Example 15 | |
|---|---|---|---|---|---|---|---|---|
| Clearing point [°C.] | +81 | | +77 | | +80 | | +60.5 | |
| $\Delta n$ | +0.2088 | | +0.1981 | | +0.2046 | | 0.2007 | |
| (589 nm, 20° C.) | | | | | | | | |
| $V_{10}$ | 2.184 | | 2.262 | | 2.313 | | 2.2007 | |
| $V_{90}/V_{10}$ | 1.107 | | 1.095 | | 1.099 | | 1.079 | |
| Composition [%]: | K6 | | PCH-3 | 8.00 | PCH-3 | 26.00 | K6 | 5.00 |
| | K9 | | BCH-32 | 8.00 | PTP-20F | 12.00 | PCH-3 | 24.00 |
| | K15 | | PTP-20F | 8.00 | PTP-40F | 8.00 | CPTP-30CF3 | 5.00 |
| | BCH-32 | | PTP-40F | 11.00 | CPTP-30CF3 | 8.00 | PTP-20F | 6.00 |
| | PCH-301 | | CPTP-30CF3 | 23.00 | CCP-20CF3 | 7.00 | PTP-40F | 6.00 |
| | PTP-20F | | PTP-102 | 7.00 | CP-30CF3 | 7.00 | PTP-102 | 5.00 |
| | PTP-40F | | PTP-201 | 7.00 | PTP-102 | 7.00 | PTP-201 | 5.00 |
| | CPTP-30CF3 | | PTP-501 | 8.00 | PTP-201 | 7.00 | PTP-501 | 6.00 |
| | PTP-102 | | PTP-502 | 4.00 | PTP-501 | 6.00 | PTP-502 | 6.00 |
| | PTP-201 | | CPTP-301 | 4.00 | PTP-502 | 3.00 | I32 | 10.00 |
| | CPTP-301 | | CCH-34 | 4.00 | SCH-32 | 10.00 | CPTP-301 | 4.00 |
| | CPTP-302 | 4.00 | | | I32 | | CPTP-302 | 4.00 |
| | CPTP-303 | 4.00 | | | | | CPTP-303 | 4.00 |
| | | | | | | | CCH-34 | 10.00 |

| | Example 16 | Example 17 | Example 18 |
|---|---|---|---|
| Clearing point [°C.] | +79 | +77 | +77 |
| $\Delta n$ | 0.2026 | 0.1975 | 0.2001 |
| (589 nm, 20° C.) | | | |
| $V_{10}$ | 2.126 | 2.126 | 2.156 |
| $V_{90}/V_{10}$ | 1.12 | 1.093 | 1.101 |

TABLE II-continued

| Composition [%]: | PCH-3 | 10.00 | K6 | 8.00 | K6 | 8.00 |
|---|---|---|---|---|---|---|
| | K6 | 8.00 | PCH-3 | 19.00 | PCH-3 | 16.00 |
| | K9 | 8.00 | CCP-20CF3 | 4.00 | CCP-20CF3 | 4.00 |
| | PYP-31 | 8.00 | CCP-30CF3 | 4.00 | CCP-30CF3 | 4.00 |
| | PTP-20F | 5.00 | CPTP-30CF3 | 5.00 | CPTP-30CF3 | 5.00 |
| | PTP-40F | 5.00 | PTP-20F | 6.00 | PTP-20F | 8.00 |
| | PTP-102 | 4.00 | PTP-40F | 5.00 | PTP-40F | 5.00 |
| | PTP-201 | 4.00 | PTP-102 | 4.00 | PTP-102 | 4.00 |
| | PTP-501 | 5.00 | PTP-201 | 5.00 | PTP-201 | 5.00 |
| | PTP-502 | 5.00 | PTP-501 | 6.00 | PTP-501 | 6.00 |
| | CPTP-301 | 5.00 | PTP-502 | 6.00 | PTP-502 | 6.00 |
| | CPTP-302 | 5.00 | CPTP-301 | 4.00 | CPTP-301 | 4.00 |
| | CPTP-303 | 5.00 | CPTP-302 | 4.00 | CPTP-302 | 5.00 |
| | CPTP-20CF3 | 7.00 | CPTP-303 | 4.00 | CPTP-303 | 4.00 |
| | CPTP-30CF3 | 7.00 | PYP-31 | 6.00 | PYP-31 | 9.00 |
| | CCH-34 | 9.00 | CCH-34 | 10.00 | CCH-34 | 9.00 |
| | (12) | (13) | (14) | (15) | (16) | (17) | (18) |
| $T_{ave}$ (ms) | 78 | 72 | 75 | 102 | 58 | 79 | 68 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A high-multiplexed supertwist liquid-crystal display containing two plane-parallel outer plates which, together with a frame, form a cell, a nematic liquid-crystal mixture of positive dielectric anisotropy which is present in the cell, electrode layers with superposed alignment layers on the insides of the outer plates which address each pixel by orthogonal row wave forms.

pre-tilt angle between the longitudinal axis of the molecules at the surface of the outer plates and the outer plates of from about 1 degree to 30 degrees, and a twist angle of the liquid-crystal mixture in the cell from alignment layer to alignment layer with a value of between 100° and 600°, wherein the nematic liquid-crystal mixture consists essentially of a) 15–50% by weight of a liquid-crystalline component A, which is one or more two- or there-ringed compounds having a dielectric anisotropy of more than +1.5;

b) 0–25% by weight of a liquid-crystalline component B, which is one or more two- or three-ringed compounds having a dielectric anisotropy form -1.5 to +1.5;

c) 40–80% by weight of a liquid-crystalline component T, which is three or more compounds having a tolan-4, 4'-diyl structure element, and d) an optically active component D in such an amount that the ratio between the layer thickness (separation of the plane-parallel outer plates) and the natural pitch of the chiral nematic liquid-crystal mixture is from about 0.2 to 1.3, wherein the nematic liquid crystal mixture has a nematic phase range of at least 60° C., a viscosity of not more than 25 mPas, a birefringence of at least 0.1950 and a dielectric anisotropy of at least +1, the dielectric anisotropies of the compounds and the parameters based on the nematic liquid-crystal mixture being based on a temperature of 20° C., and wherein component T comprises at least three compounds of formula I

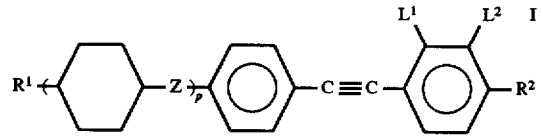

in which $R^1$ is alkyl, alkoxy, alkenyl or alkenyloxy with 1 to 8 C atoms, $L^1$ and $L^2$ are each independently H or F, $R^2$ is F, $OCF_3$, alkyl or alkoxy with 1 to 8 C atoms, Z is a single bond, and p is 0 or 1.

2. A display according to claim 1, wherein component A contains at least one compound of formulae II or III, wherein R is alkyl, alkoxy, alkenyl or alkenyloxy with up to 12 C atoms,

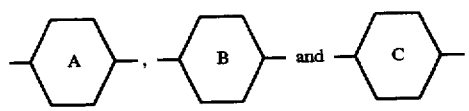

are each independently

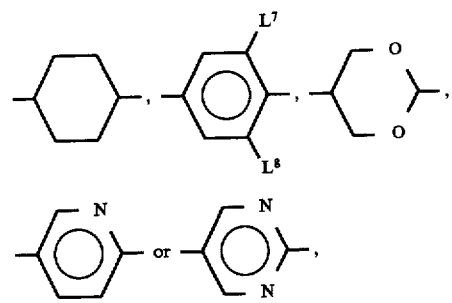

$L^3$ through $L^8$ are each independently H or F,
$Z^1$ is —COO—, —CH$_2$CH$_2$— or a single bond,
$Z^2$ is —COO—, —CH$_2$CH$_2$—, —C≡C or a single bond,
Q is CF$_2$, OCF$_2$, CFH, OCFH or a single bond,
Y is F or Cl,
m is 1 or 2, and
n is 0 or 1.

3. A display according to claim 2, wherein component A contains at least one compound of the formulae IIa to IId:

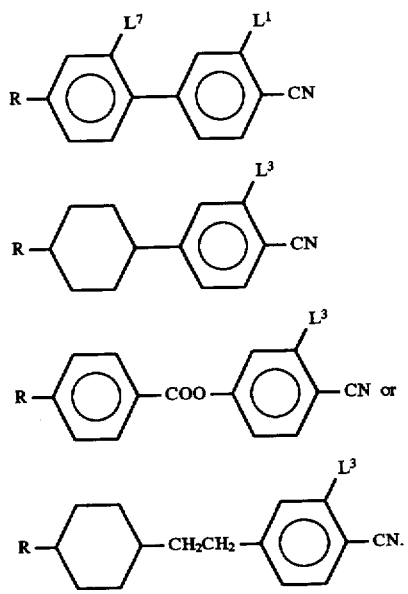

4. A display according to claim 1, wherein component B contains at least one compound of IV1 to IV7:

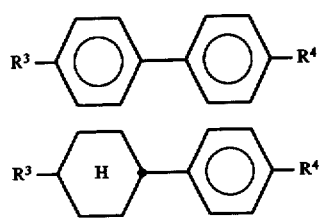

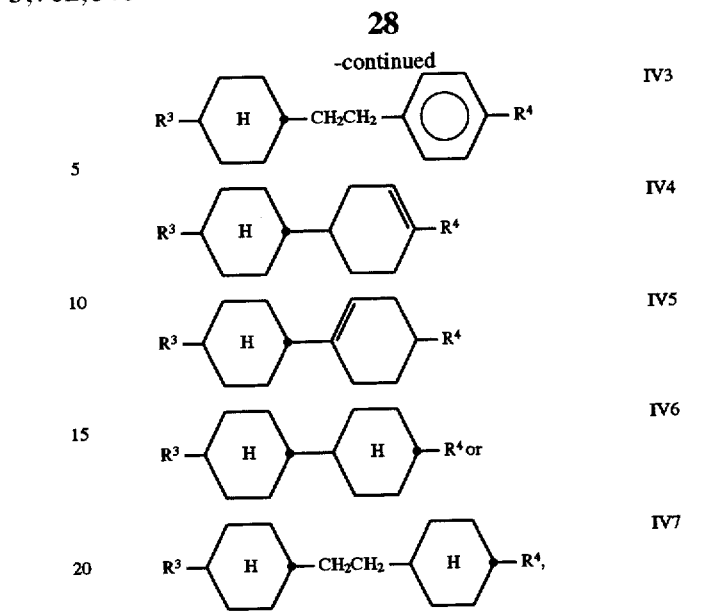

and $R^3$ and $R^4$ are alkyl, alkenyl or alkenyloxy with up to 12 carbon atoms.

5. A display according to claim 1, wherein component B contains at least one compound of IV8 to IV21:

in which the 1,4-phenylene groups IV7 to IV17 and IV21 may each, independently of one another, also be mono-or polysubstituted by fluorine.

6. A display according to claim 1, wherein component T contains five or more compounds of Ia to Ie:

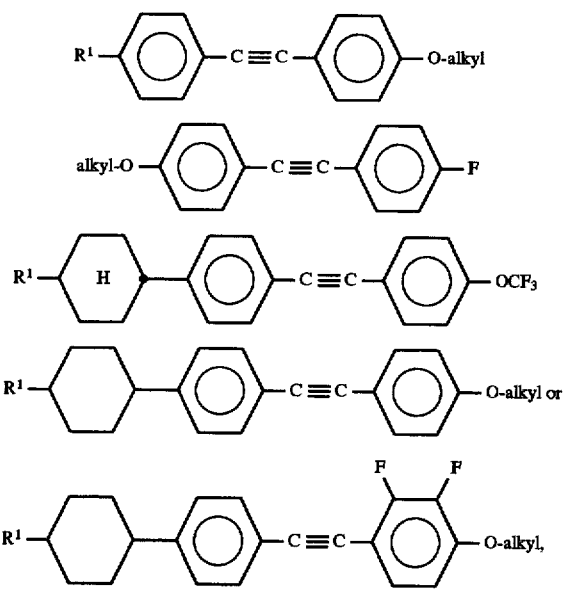

in which alkyl is n-alkyl with 1 to 8 carbon atoms.

7. A display according to claim 1, wherein component T contains one or two compounds of formula Ia1

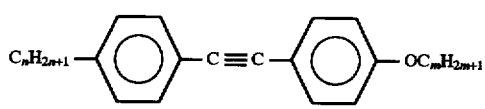

in which n and m are each independently 1 or 2.

8. A display according to claim 1, wherein the nematic liquid crystal mixture contains 30–60% by weight of at least one compound of formula Ia

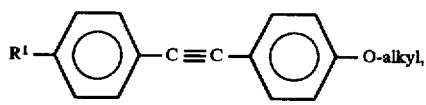

in which alkyl is n-alkyl with 1–8 carbon atoms.

9. A display according to claim 2, wherein the nematic liquid crystal mixture contains 15–50% by weight of liquid crystalline compound A, consisting essentially of compounds of formula III, and at least 30–50% by weight of at least one compound of formula I wherein $R^2$ is F or $OCF_3$.

10. A display according to claim 1, wherein the liquid crystal mixture has an optical anisotropy An of greater than 0.200.

11. A liquid-crystal mixture consisting essentially of a) 15–50% by weight of a liquid-crystalline component A, which is one or more two- or there-ringed compounds having a dielectric anisotropy of more than +1.5;

b) 0–25% by weight of a liquid-crystalline component B, which is one or more two- or three-ringed compounds having a dielectric anisotropy form −1.5 to +1.5;

c) 40–80% by weight of a liquid-crystalline component T, which is three or more compounds having a tolan-4, 4'-diyl structure element, and d) an optically active component D in such an amount that the ratio between the layer thickness (separation of the plane-parallel outer plates) and the natural pitch of the chiral nematic liquid-crystal mixture is from about 0.2 to 1.3, wherein the nematic liquid crystal mixture has a nematic phase range of at least 60° C., a viscosity of not more than 25 mPas, a birefringence of at least 0.1950 and a dielectric anisotropy of at least +1, the dielectric anisotropies of the compounds and the parameters based on the nematic liquid-crystal mixture being based on a temperature of 20° C., and wherein component T comprises at least three compounds of formula I

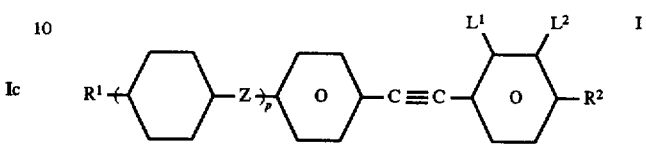

in which $R^1$ is alkyl, alkoxy, alkenyl or alkenyloxy with 1 to 8 C atoms, $L^1$ and $L^2$ are each independently H or F, $R^2$ is F, $OCF_3$, alkyl or alkoxy with 1 to 8 C atoms, Z is a single bond, and p is 0 or 1.

12. A method for improving the switching times and steepness of STN-displays in which each pixel is addressed by an orthogonal row wave form, comprising including in said display a liquid crystalline mixture containing at least one compound

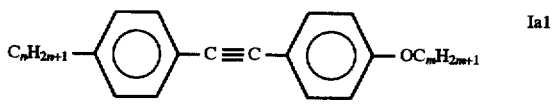

wherein n and m are each independently 1 or 2.

13. A display according to claim 1, comprising 40% to 80% by weigh of at least three compounds of formula I, and 5% to 15% by weight of at least one compound of formula IV6

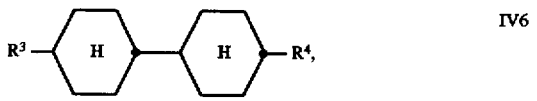

and $R^3$ and $R^4$ are alkyl, alkoxy, alkenyl or alkenyloxy with up to 12 carbon atoms.

14. A high-multiplexed supertwist liquid-crystal display containing two plane-parallel outer plates which, together with a frame, form a cell, a nematic liquid-crystal mixture of positive dielectric anisotropy which is present in the cell, electrode layers with superposed alignment layers on the insides of the outer plates which address each pixel by orthogonal row wave forms, pre-tilt angle between the longitudinal axis of the molecules at the surface of the outer plates and the outer plates of from about 1 degree to 30 degrees, and a twist angle of the liquid-crystal mixture in the cell from alignment layer to alignment layer with a value of between 100° and 600°, wherein the nematic liquid-crystal mixture consists essentially of a) 15–50% by weight of a liquid-crystalline component A, which is one or more two- or there-ringed compounds having a dielectric anisotropy of more than +1.5;

b) 0–25% by weight of a liquid-crystalline component B, which is one or more two- or three-ringed compounds having a dielectric anisotropy form −1.5 to +1.5;

c) 42–80% by weight of a liquid-crystalline component T, which is three or more compounds having a tolan-4,4'-diyl structure element, and d) an optically active component D in such an amount that the ratio between the layer thickness (separation of the plane-parallel outer plates) and the natural pitch of the chiral nematic liquid-crystal mixture is from about 0.2 to 1.3, wherein the nematic liquid crystal mixture has a nematic phase range of at least 60° C., a viscosity of not more than 25 mPas, a birefringence of at least 0.1950 and a dielectric anisotropy of at least +1, the dielectric anisotropies of the compounds and the parameters based on the nematic liquid-crystal mixture being based on a temperature of 20° C., wherein component T comprises at least three compounds of formula I $$R^1-\text{Cy}-(Z)_p-\text{Ph}-C\equiv C-\text{Ph}(L^1)(L^2)-R^2 \quad I$$

in which $R^1$ is alkyl, alkoxy, alkenyl or alkenyloxy with 1 to 8 C atoms, $L^1$ and $L^2$ are each independently H or F, $R^2$ is F, $OCF_3$, alkyl or alkoxy with 1 to 8 C atoms, Z is a single bond, and p is 0 or 1, and wherein component B contains at least one compound of IV1 to IV4:

$$R^3-\text{Cy}(O)-\text{Cy}(O)-R^4 \quad IV1$$

$$R^3-\text{Cy}(H)-\text{Ph}(O)-R^4 \quad IV2$$

$$R^3-\text{Cy}(H)-CH_2CH_2-\text{Ph}(O)-R^4 \quad IV3$$

$$R^3-\text{Cy}(H)-\text{Cy}^=-R^4 \quad IV4$$

in which $R^3$ and $R^4$ are alkyl, alkoxy, alkenyl or alkenyloxy with up to 12 carbon atoms, with the proviso that the mixture contains 5% to 15% by weight of at least one compound of formula IV6

$$R^3-\text{Cy}(H)-\text{Cy}(H)-R^4. \quad IV6$$

15. A display according to claim 1, wherein in at least one compound of formula I, p is 1.

16. A display according to claim 1, wherein p is 1.

17. A liquid crystal mixture according to claim 11, wherein at least one compound of formula I, p is 1.

18. A liquid crystal mixture according to claim 11, wherein p is 1.

* * * * *